United States Patent [19]

Gettleman et al.

[11] Patent Number: 4,543,379
[45] Date of Patent: Sep. 24, 1985

[54] SOFT AND FIRM DENTURE LINER FOR A COMPOSITE DENTURE AND METHOD FOR FABRICATING

[75] Inventors: Lawrence Gettleman, Metairie, La.; Charles L. Farris, Satellite Beach, Fla.; H. Ralph Rawls; Ralph J. LeBouef, Jr., both of New Orleans, La.

[73] Assignee: Gulf South Research Institute, Baton Rouge, La.

[21] Appl. No.: 559,277

[22] Filed: Dec. 8, 1983

Related U.S. Application Data

[62] Division of Ser. No. 432,248, Oct. 1, 1982, Pat. No. 4,432,730.

[51] Int. Cl.$^4$ .............................................. A61K 6/08
[52] U.S. Cl. ..................................... 523/120; 106/35; 433/168.1
[58] Field of Search ....................... 433/168, 180, 171; 106/35; 523/120

[56] References Cited

U.S. PATENT DOCUMENTS

| | | | |
|---|---|---|---|
| 3,702,833 | 11/1972 | Rose et al. | 528/399 |
| 3,888,799 | 6/1975 | Rose et al. | 528/399 |
| 3,945,966 | 3/1976 | Vicic et al. | 528/399 |
| 4,251,215 | 2/1981 | May et al. | 433/168 |
| 4,433,958 | 2/1984 | Fellman et al. | 433/199 |

Primary Examiner—Lorenzo B. Hayes
Attorney, Agent, or Firm—Martin P. Hoffman; Jean A. Buttmi; Mitchell B. Wasson

[57] ABSTRACT

The invention provides a denture liner composition for a composite denture based on a phosphonitrilic fluoroelastomer (poly(fluoroalkoxy)phosphazene) curable at atmospheric pressure at temperatures of 100° C. or less, conveniently by immersing the packed denture flask in a water bath at the appropriate temperature. The composition includes filler materials for increasing the hardness of the cured liner, interpenetrating polymers for increasing firmness and bond strength, and cross-linking agents for increasing the tensile strength and bond strength of the cured liner. The composite denture is preferably prepared in a one-step process wherein the liner composition material of a single firmness is cured in situ with the denture base material. Alternatively, a firm liner material may be cured at the periphery of the denture and a softer liner material cured at the center, in order to provide a firm elastic liner where adjustments must be made by grinding and where the patient's soft tissues must be displaced, and a soft elastic liner over the bony anatomy of the patient where stresses from chewing are most concentrated and the soft tissues are thin.

9 Claims, 3 Drawing Figures

SOFT AND FIRM DENTURE LINER FOR A COMPOSITE DENTURE AND METHOD FOR FABRICATING

GRANT INFORMATION

The development of the invention was supported by the National Institute of Dental Research through Research Grant Number 1R01 DE-04814.

This is a division of application Ser. No. 06/432,248 filed Oct. 1, 1982, now U.S. Pat. No. 4,432,730.

BACKGROUND OF THE INVENTION

Prosthetic dentures currently in use typically consist of a baseplate of hard poly(methyl methacrylated) which supports the artificial teeth needed for chewing and for esthetics. Many patients have difficulty tolerating a hard denture so there is a need for a soft denture liner affixed to the denture base to cushion the soft tissue. A number of criteria have been established for materials to be useful as denture liners, notably non-toxicity and non-allergenicity. The best materials should be permanently resilient, inert, cleanable, and substantially water-insoluble, and have low water-sorption characteristics. While softness is desirable for comfort, the liner material must be sufficiently firm to displace the soft tissues of the mouth and to allow grinding of the denture periphery to avoid creating sore spots; additionally, the liner material must be permanently bondable to the denture base material. It is also highly preferably from a practical standpoint that the lined denture be capable of fabrication under conditions generally found in dental laboratories, or in a dentist's office, avoiding extremes of temperature and pressure conditions, or the use of special equipment.

Several liner materials have been proposed which satisfy these criteria sufficiently to be useful, such as silicone rubber, plasticized poly(methyacrylates), polyurethanes, and polyvinyl chlorides. An especially useful liner material is disclosed in U.S. Pat. No. 4,251,215 issued on Feb. 17, 1981 to May et al., comprising phosphonitrilic fluoroelastomer (poly(fluoroalkoxy)phosphazene) which exhibits particularly good resiliency, water-sorption, and biocompatibility characteristics. The fluoroelastomer liner materials exemplified therein, however, have been found to be somewhat deficient with respect to tensile strength, hardness, and bondability to denture base material, as compared to the theoretical ideal. Further, the process for forming the denture as described in the May et al. patent is a two-step process which requires the liner and denture base to be separately cured, and additionally requires the use of strong bonding agents, as well as the use of temperatures in excess of 100° C. (boiling point of water at atmospheric pressure) for curing the liner. The fabrication of this prior art composite denture thus requires somewhat elaborate equipment, and cannot be conveniently accomplished in an average dental office or laboratory.

SUMMARY OF THE INVENTION

The invention accordingly provides a denture liner composition based on phosphonitrilic fluoroelastomers (poly(fluoroalkoxy)phosphazenes) which, when cured by crosslinking of pendant groups, retain the excellent liner properties of the fluoroelastomer base material, while exhibiting improved hardness, tensile strength, grinding and adjusting ability, and bond strength characteristics. The denture liner composition is curable at or below temperatures of 100° C. at atmospheric pressure, and retains its dimensional stability during curing. Thus, according to the process of the invention, the composite denture is formed by curing the shaped liner material in situ, placed directly against a conventional denture base material, conveniently by immersing the packed denture flask in an open water bath at boiling temperatures. The method improves the bond strength of the finished composite denture, and obviates the use of potentially harmful bonding agents such as sulfuric or perfluoroacetic acid or epoxy or urethane adhesives. Most importantly, the method avoids the use of high temperatures and/or pressurized equipment, and can thus be used in average commercial dental laboratories or even in the average dentist's office. Additionally, the use of low temperatures avoids vaporization of monomers such as methyl methacrylate, and prevents dehydration of the liner material during curing. Dehydration necessitates rehydration of the liner prior to use in the intended aqueous environment, and the dehydration/rehydration steps may cause undesirable dimensional changes in the liner as well as the substrate denture base.

Broadly, the composition of the invention comprises a phosphonitrilic fluoroelastomer and interpenetrating lower alkyl methacrylate monomer to improve hardness of the product liner and bond strength of the fluoroelastomer to the denture base. The composition preferably further includes a dimethacrylate glycol ester cross-linking agent such as polyethylene glycol dimethacrylate, 1,6-hexamethylene glycol dimethacrylate, ethylene glycol dimethacrylate, or tetraethylene glycol dimethacrylate to improve tensile strength and bond strength of the product liner. Filler particles such as particles of a hard acrylic resin, silica, $Al_2O_3$, diatomaceous earth, or $BaSO_4$ are also optionally included to increase hardness. The composition further includes curing additives to facilitate curing of the liner material at tempratures at or below 100° C., particularly benzoyl peroxide or lauroyl peroxide as free-radical initiator and MgO as an acid scavenger. The following materials, in admixture, are within the scope of the invention:

| Material | Percent by Wt. of Total Composition |
| --- | --- |
| Phosphonitrilic fluoroelastomer | 30 to 98 |
| Filler | 0 to 30 |
| Interpenetrating monomer | 1 to 40 |
| Cross-linker | 0 to 20 |

DETAILED DESCRIPTION OF THE INVENTION

Figure 1:
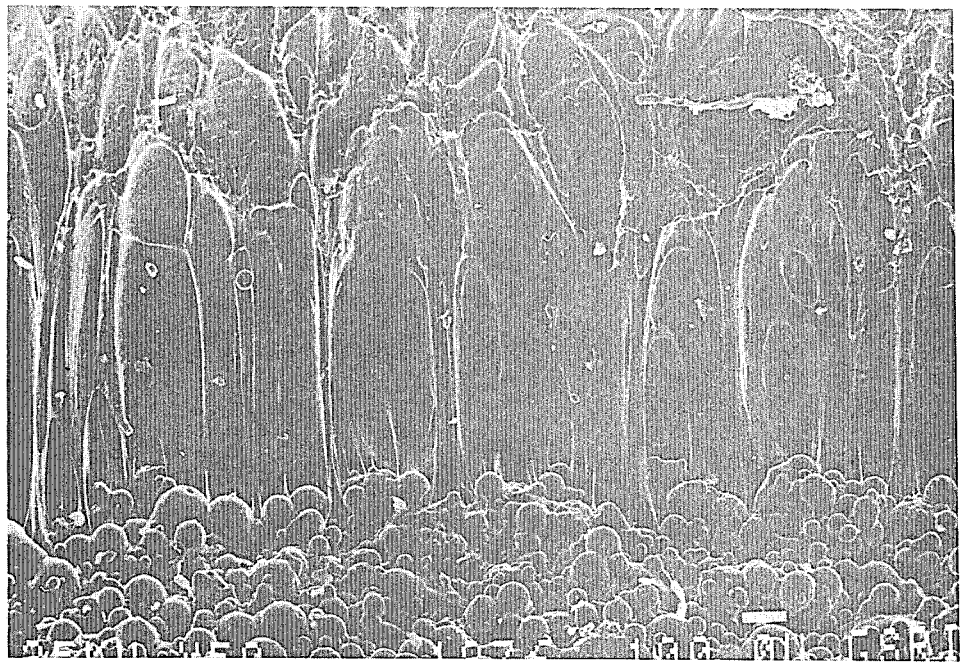
FIG. 1 is an SEM photomicrograph (50×original magnification) illustrating a 180° peel test on a PNF-200 dental liner composition without filler.

The dental liner composition of the invention is based on phosphonitrilic fluoroelastomers (poly(fluoroalkoxy)phosphazenes) of the type described in U.S. Pat. Nos.

3,702,833 and 3,888,799, both to Rose et al. The polymers are characterized by repeating units of the general formula

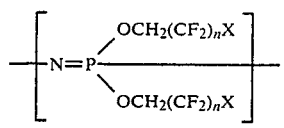

wherein X is H or F, and n is usually from 1 to 11. Such elastomers are commercially available, and are typified by PNF-200, available from Firestone Central Research Laboratories, 1200 Firestone Parkway, Akron, Ohio. This material is represented as

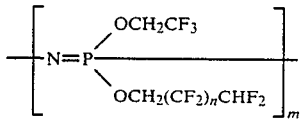

wherein n is 3, 5, 7, 9, or 11, and m is from 10,000 to 50,000, and described as a thermoset having the following properties:

| | |
|---|---|
| Color | Amber |
| Specific Gravity | 1.75 to 1.85 |
| Mooney Viscosity | 15 |
| Solvents | Ketones, THF, DMF |
| Glass Transition Temperature | $-68°$ C. ($-90°$ F.) |
| Durometer A Hardness | 35–90 |
| Tensile Strength | 1000–2000 psi |
| 100% Modulus | 400–2000 psi |
| Elongation | 75–250% |
| Tear Resistance | to 250 ppi |

Preferably, the fluoroelastomer is purified by extraction and coagulation from methanol in a known manner prior to biomedical use in the liner composition.

The elastomer is employed in amounts of from about 30% to about 98% by weight of the total composition, usually from about 30% to 60% for a firm liner material, and from about 40% to about 95% for a soft liner material.

According to the invention, the fluoroelastomer is compounded with interpenetrating methacrylate monomers comprising $C_1$–$C_6$ alkyl methacrylate monomers such as cyclohexyl methacrylate, butyl methacrylate, or, especially, methyl methacrylate monomer (MMA), which unexpectedly improve bond strength and tensile strength, and provide good hardness and elongation in the liner material. The interpenetrating monomers are compounded with the fluoroelastomer gum in an amount of from about 1% to about 40% by weight of monomer, based on the weight of the total composition. Preferably, the monomer is compounded with the elastomer by incorporating a sufficient amount of fluoroelastomer into the liquid monomer to form a viscous syrup; the syrup is then incorporated into the remainder of the fluoroelastomer as by milling, conveniently on a low speed mill such as a Farrel rubber mill, without heating. Alternatively, the monomer may be placed in an airtight container (to prevent evaporation of the monomer) for a period of from about 48 to 72 hours, or until the monomer has completely interpenetrated the elastomer. Additional monomer may be added to increase firmness, if desired, or monomer may be evaporated for a softer product.

In one embodiment of the invention, the liner composition further includes a cross-linking agent compounded with the monomer and fluoroelastomer gum comprising a dimethacrylate glycol ester cross-linking agent, preferably ethylene glycol dimethacrylate (EGDMA), in order to improve tensile and bond strength of the liner product. Generally, an amount of cross-linking agent of from about 0% to about 20%, preferably from about 1% to about 12.5%, by weight of the total composition is employed, with amounts at the lower end for a soft product and at the higher end for a firm product. The effects on bond strength of PNF-200 obtained with a series of methacrylate cross-linking agents, stoichiometrically adjusted for bonding sites, are set forth in Table I. All the dimethacrylates tested usefully improved bond strength, while a significant improvement in bond strength was obtained with EGDMA. All bond strength tests were conducted according to ASTM D 903.

TABLE I

| Methacrylate Cross-linker | Wt % | N | Bond Strength N/m | |
|---|---|---|---|---|
| Control (PNF-200) | — | 5 | 1280 | } * |
| n-Lauryl Methacrylate | 10 | 4 | 1140 | |
| Polyethylene Glycol 200 Dimethacrylate | 12 | 3 | 1670 | } * |
| 1,6-Hexamethylene Glycol Dimethacrylate | 10 | 5 | 1810 | } * |
| Tetraethylene Glycol Dimethacrylate | 8 | 4 | 2160 | |
| Ethylene Glycol Dimethacrylate (EGDMA) | 10 | 5 | 3590 | |

*NSD at $P \leq 0.05$, Scheffe

The adhesion of PNF-200 compounded with 10% EGDMA is illustrated in FIG. 1, showing the peel zone wherein the liner has been peeled from the denture base in the cured composite denture.

The improved bond strength and firmness obtained with both EGDMA and MMA is set forth in Table II (all amounts are in percent by weight of total composition).

TABLE II

| PNF | MMA | EGDMA | Hardness (Durometer A) | *Bond Strength (N/m) |
|---|---|---|---|---|
| 58 | 36 | — | 13.4 | 3835 |
| 51 | 36 | 8.6 | 38.6 | 7250 |

*ASTM Peel Test, scaled.

Tensile strengths of about 7.0 MPa and 406% elongation have been achieved.

The liner composition of the invention further may include a filler material homogeneously admixed with the purified fluoroelastomer gum. If a filler is employed, the filler is first preferably dispersed in the interpenetrating monomer, prior to compounding with the fluoroelastomer. A portion of the fluoroelastomer, typically about 10% by weight, is then incorporated into this dispersion to form a syrup, as previously described. A very uniform dispersion of the filler particles is thus obtained after milling the remainder of the elastomer with the syrup. A particularly rapid compounding is obtained if a portion of the monomer is employed to pre-soften the remainder of the elastomer. In dentures prepared according to the process of the invention wherein the liner material is cured in situ on the denture base material, the filler particles significantly increase the strength of the bond between the liner and base owing to stiffening of the rubber or the mechanical interlocking of these particles with the liner and base material during curing; (see FIGS. 1–3). Particles comprising beads or fibers are suitable, and it is generally preferable that the particles be compatible with the denture base dough to promote adhesion during the curing process. LUCITONE 199 beads or fibers, obtainable from the L.D. Caulk Company (a division of Dentsply International, Inc.), Milford, Del., are exemplary acrylic particles useful in the composition of the invention. These particles are derived from a hard poly(methyl methacrylate) resin, and are particularly useful in conjunction with LUCITONE 199 denture base acrylic dough, a partially-cured grafted poly(methyl methacrylate) thermoset, similarly obtainable. Other fillers or extenders that may be included comprise hydrophobic amorphous silica of very small particle size. These materials reduce the amount of PNF required, increase hardness, and may improve bond strength. Two examples of these fumed silica fillers/extenders are Quso WR-542, PQ Corp., Valley Forge, PA, a silica washed with silicone oil, and Tullanox 500, Tulco, No. Billerica, MA, a silica coated with trimethyl chlorosilane. A particularly useful filler material is barium sulfate, which renders the dental liner radiopaque and detectable on radiographs if a portion should be swallowed or inhaled. (see FIG. 2).

The amount of filler material employed in the liner composition will vary according to the desired hardness of the finished liner material. While large amounts of poly(methyl methacrylate) particles (up to 28% by weight of the composition) were found to result in decreased elongation, increased amounts of filler over about 10% by weight of the composition had little effect on bond strength or tensile strength (Table IV), while effecting a more or less proportional increase in firmness of the finished product. Accordingly, useful amounts of polymeric filler are from about 7% by weight of the composition, for a soft product, to about at least 30% by weight of the composition for a firm product. Preferably, from about 0% to about 10% by weight of inorganic filler is employed for a soft product, and most preferably, about 0–5% by weight for a soft product and about 10–20% by weight for a firm product, depending on which filler is used.

Figure 3:
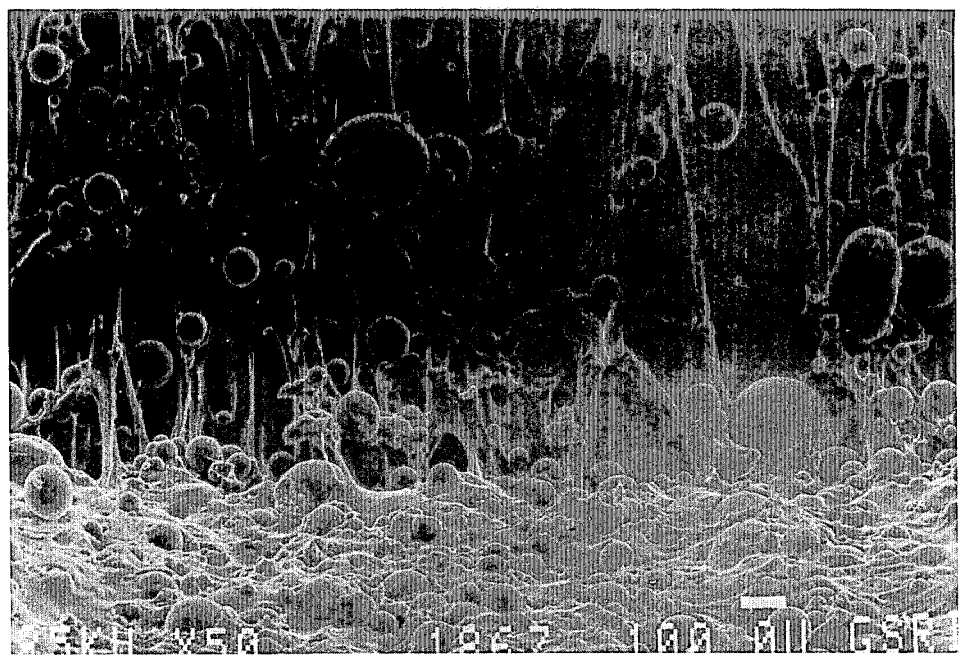
FIG. 3 is similar to FIG. 1, illustrating a 180° peel test on a PNF-200 dental liner composition with PMMA filler.

The effect of various fillers on tensile strength, elongation, and hardness of a PNF-200 control is set forth in Table III, infra. All the fillers decreased tensile strength. Increased bond strength of a PNF-200/PMMA composition is summarized in Table IV, infra, and illustrated in FIG. 3, showing the "peel zone" wherein the filled PNF-200 liner has been peeled from the poly(methyl methacrylate) denture base after curing. Adhesion is imparted by mechanical interlocking of the elastomer around the PMMA beads, which in turn are locked into the polymerized denture base dough. The peel test employed is the Wright characterization of the adhesion of soft lining materials to poly(methyl methacrylate) (J. Dent. Res. 61:1002–1005, 1982).

TABLE III

| Filler Agent | Wt % | N | Tensile Strength (MPa) | Elongation (%) | Durometer A Hardness |
|---|---|---|---|---|---|
| Control (PNF-200) | 0 | 5 | 1.5 | 171* | 17 |
| Aluminum Oxide | 20 | 5 | 0.27 | 125 | 25 |
| Silanized Syloid | 20 | 5 | 0.61* | 282 | 45 |
| Diatomaceous Earth | 20 | 5 | 0.81 | 598 | — |
| Poly(methyl methacrylate)(PMMA) | 10 | 5 | 0.82 | 740 | 38 |

*NSD P ≦ 0.05, Scheffe

The effects of varying amounts of EGDMA and PMMA beads on bond strength, hardness, tensile strength and elongation of the dental liner composition are set forth in Table IV. EDGMA cross-linker significantly improves bond strength, especially in amounts of about 10% by weight of the composition, and further improves tensile strength, especially in amounts of about 20% by weight of the composition. Unfavorable losses in tensile strength owing to the presence of filler in the liner composition are compensated by the presence of dimethacrylate cross-linker in suitable amounts.

TABLE IV

| EGDMA (Wt %) | PMMA (Wt %) | N | Bond Strength (N/m) | Durometer A Hardness | Tensile Strength (MPa) | N | Elongation (%) |
|---|---|---|---|---|---|---|---|
| 0 | 0 | 5 | 1280* | 17 | 1.5* | 5 | 171 |
| 5 | — | 4 | 2750 | 43 | 1.3 | 4 | 674 |
| 10 | — | 5 | 3590 | 48 | 1.8 | 4 | 489 |
| 20 | — | 4 | 2980* | 55 | 3.1* | 4 | 428 |
| — | 7 | 4 | 1420 | 38 | 0.87 | 4 | 740 |
| — | 28 | 4 | 1610 | 55 | 0.77 | 4 | 368 |

*NSD P ≦ 0.05, Scheffe

The effects of EGDMA and PMMA beads on tensile set of PNF-200 is set forth in Table V.

Tensile set was measured by straining flat tensile bar specimens 50% and then holding them either dry or in Silverstone's artificial saliva for $10^3$ seconds. The specimen was then released and allowed to recover. Tensile set was measured at $10^3$ seconds and $8.6 \times 10^4$ seconds (24 hours) as shown in Table V. It is readily apparent that the addition of 28% PMMA greatly reduces tensile set, but EGDMA had no effect as an additive to PNF-200.

TABLE V

| Tensile Set in %. n = 7 to 10 | PNF-200 | | | | |
|---|---|---|---|---|---|
| | PMMA Beads | | EGDMA | | |
| | 7% | 28% | 5% | 10% | 20% |
| Unrecovered Elongation after $10^3$ sec | 18.9* | 7.6 | 19.3* | 20.4* | 19.1 |
| Unrecovered Elongation after $8.6 \times 10^4$ sec (24 h) | #6.9* | 3.6 | 6.9* | 7.6* | 7.5 |

NSD, $P \leq 0.05$ between samples in each row. ASTM D 412, in artificial saliva
Dry In addition to the filler materials, monomers, and dimethacrylate cross-linking agents, other components commonly incorporated into dental liners may be compounded with the fluoroelastomer base. In particular, pigments making the liner more visually acceptable may be used, such as iron oxide based pigments, and Cd-S-SE pigments.

The composite denture of the invention is broadly formed by compounding fluoroelastomer with the components of the dental liner composition as previously described, pressing the resulting composition into a wafer, and molding after removal of a spacer to a denture base dough packed in a customary mold flask; the composite denture is then heat-treated to cure the liner and the denture base dough together to provide a lined denture. In an exemplary procedure, the ingredients are milled at least ten minutes on a cold rubber mill, and the liner composition is then pressed flat into sheets of the desired thickness, generally about 2 mm to 3 mm. A denture waxing is boiled out of a flask in the usual fashion, and fresh denture base dough is packed. A 1 to 2 mm spacer is placed on the tissue side of the mold cavity, with polyethylene sheet spacers in place, and the denture flask trial-packed several times. Sheets of the soft liner composition are then laid against the base material, cut to shape, and the flask is again trial-packed. The denture flask is then closed under pressure (about 20.7 MPa), and the composite denture is heat-treated to cure the base and liner material, for example, first at 73° C. for 1.5 hours, and then at 100° C. for up to about 1.5 hours.

In one advantageous embodiment of the invention, a wafer of firm liner material is completely laid over the base material dough and trial-packed; the central area of the liner over the alveolar ridges is outlined and cut away. Soft liner material is then laid in the cut-away central area, and the flask is again trial-packed. The composite denture is then heat-cured. This embodiment provides a firm, creep-resistant, higher-strength material at the periphery of the denture which is polishable, adjustable, and properly displaces underlying soft tissue, while providing a soft, creep-deformable lower-strength material forming a soft cushion at the center of the denture over the bony structures of the jaw.

While this process provides good bond strength between the denture liner and denture base, it is advantageous to maximize adhesion between the components of the composite denture, in the finished product. A particularly suitable method is to liberally apply acrylic monomer between the liner and base material prior to curing. A particularly preferred monomer for use with PMMA dough is methyl methacrylate (MMA), for example, LUCITONE 199 denture base monomer.

In a particular preferred embodiment of the process of the invention, a known free radical initiator such as lauroyl or benzoyl peroxide and an acid scavenger such as magnesium oxide are incorporated into the liner composition. The use of each of these materials in amounts of from about 1% to 2% by weight of the total composition permit the curing of the composition denture at temperatures of 100° C. or less, conveniently by placing the packed flask in a water-bath at atmospheric pressure. The exact conditions will depend on the particular materials employed; however, for a PMMA dough denture base of the type described herein, curing at 73° C. (165° F.) for at least one and one-half hour, followed by bringing the temperature of the water bath to 100° C. (212° F.) for a period of time up to about one and one-half hour, has been found suitable. While pressures inside the flask are initially about 3000 psig, pressurized vessels are not necessary for effecting a cure of the product.

EXAMPLE I

A soft denture liner according to the invention is prepared in the following manner:

880 g. phosphonitrilic fluoroelastomer (PNF-200) is extracted and coagulated from methanol solution to eliminate impurities, and 10 g. lauroyl peroxide added as chain initiator. The initiator is then milled into the elastomer on a rubber mill until the material appears homogeneous, and 10 g. MgO as acid scavenger are added. The material is again milled until a homogeneous mixture is obtained. 50 g. poly(methyl methacrylate) filler powder (LUCITONE 199 beads and fibers) and 50 g. ethylene glycol dimethacrylate (EGDMA) are then milled into the rubber compound. All milling is done at room temperature.

The milled PNF soft liner material is pressed into a sheet 2 to 3 mm thick using an aluminum mold and polyethylene separators, at 34.5 MPa (5000 psig) for about 15 minutes. The sheet is then cut to size with scissors for application to a poly(methyl methacrylate) denture base dough (PMMA dough) in a denture flask.

The formed liner and denture base dough are each liberally brushed with methyl methacrylate monomer on their bonding surfaces, and PNF soft liner material is trial-packed in the denture flask until the desired conformation is obtained. Firm liner material may be retained at the periphery of the denture but removed from the center, and soft liner material placed over areas of bony anatomy. The liner is then final-packed at 20.7 MPa (3000 psig) in preparation for curing. Following packing, the liner composition and denture base are cured by immersing the flask in a water bath for 90 minutes at 73° C. (165° F.); the water is then brought to a boil and curing continued for up to an additional 90 minutes. The cured composite denture is then cooled and removed from the flask. The adhesion imparted by the poly(methyl methacrylate) filler powder is illustrated in FIG. 3, showing the peel zone wherein the liner has been peeled from the denture base of the cured composite denture.

EXAMPLE II

A dental liner composition comprising 58 parts of the PNF-200 phosphonitrilic fluoroelastomer compounded with lauroyl peroxide and MgO (no filler or EGDMA) from Example I, and 36 parts methyl methacrylate monomer (MMA) was prepared in the following manner:

8 parts of the compounded PNF-200 were dissolved in the MMA by stirring to form a viscous syrup. The syrup was then rolled into the remainder of the PNF on a low-speed Farrel rubber mill, without heating, until a homogeneous product liner material was obtained. The material was then packed and cured as described in Example I. Physical characteristics of the resultant product are given in Table II, supra.

EXAMPLE III

The procedure of Example II was followed, except 8.6 parts of ethylene glycol dimethacrylate (EGDMA) were first dispersed in the liquid monomer, prior to incorporation of 8 parts PNF. Physical characteristics of the product liner material, packed and cured as described in Example I, are also given in Table II. Adhesion of the dental liner to the cured composite denture is illustrated in FIG. 1, showing the peel zone wherein the liner has been peeled from the denture base.

EXAMPLE IV

A firm dental liner composition was prepared from the following materials (all amounts are expressed in % wt. of total composition):

| PNF | MMA | EGDMA | BaSO4 | MgO | Pigment (Cd—S—Se) | Lauroyl Peroxide |
| --- | --- | --- | --- | --- | --- | --- |
| 32.25 | 38.75 | 6.0 | 20.0 | 1.5 | Trace | 1.5 |

The EGDMA, lauroyl peroxide, MgO, barium sulfate, and the pigment were evenly dispersed into the methyl methacrylate monomer, using a blender. To this dispersion was added about 8% of the total amount of PNF to form a viscous syrup of about the consistency of maple syrup. The syrup was milled into the remainder of the PNF to form a homogeneous liner composition, which was packed and cured as in Example I. The cured liner had the following characteristics:

| Tensile Strength (MPa) | Elongation % | Durometer A Hardness | Bond Strength (N/m) |
| --- | --- | --- | --- |
| 1.65 | 174 | 43 | 4482 |

Figure 2:
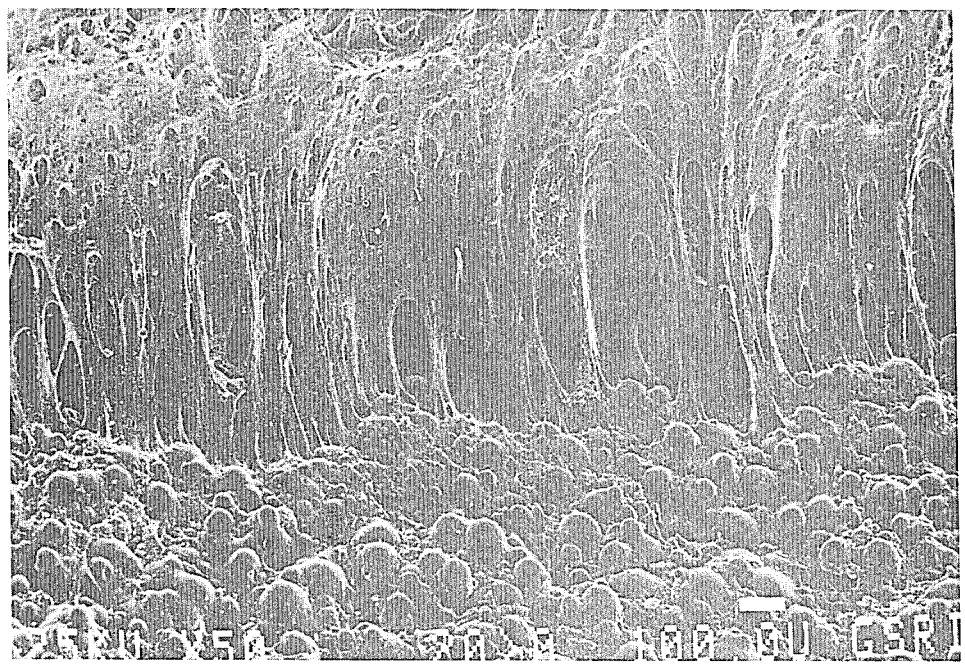
FIG. 2 is similar to FIG. 1, illustrating a 180° peel test on a PNF-200 dental liner composition with $BaSO_4$ filler.

The adhesion inparted by BaSO, to the liner composition is illustrated in FIG. 2, showing the peel zone wherein the liner has been peeled from the denture base of the cured composite denture.

EXAMPLE V

The procedure of Example IV was followed, except 30% by volume of the MMA was reserved to pre-soften the remainder portion of the PNF. Process time for compounding the PNF and syrup was signficantly shorter to achieve a homogeneous product.

EXAMPLE VI

A soft dental liner composition was prepared according to Example IV using the following materials (all amounts are expressed in percent by weight of total composition):

| PNF | MMA | EGDMA | BaSO4 | MgO | Pigment (Cd—S—Se) | Lauroyl Peroxide |
| --- | --- | --- | --- | --- | --- | --- |
| 46.25 | 38.75 | 2.0 | 10.0 | 1.5 | Trace | 1.5 |

The cured liner had the following characteristics:

| Tensile Strength (MPa) | Elongation % | Durometer A Hardness | Bond Strength (N/m) |
| --- | --- | --- | --- |
| 1.44 | 307 | 21 | 3604 |

While the application has discussed crosslinkers of dimethacrylates, the use of diacrylates are also contemplated.

What is claimed is:

1. A denture liner curable in situ with a denture base material comprising a phosphonitrilic fluoroelastomer, a $C_1$-$C_6$ alkyl methacrylate monomer, and a cross-linking agent comprising a glycol ester of dimethacrylic acid.

2. The liner of claim 1 wherein the fluoroelastomer is present in an amount of from about 30% to about 98% by weight of the total composition, the monomer is present in an amount of from about 1% to about 40% by weight of the total composition, and the cross-linkng agent is present in an amount of from about 1 to about 12.5%.

3. The denture liner of claim 2, wherein the fluoroelastomer is characterized by a plurality of repeating units of the general formula

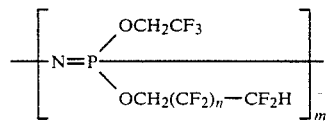

wherein n is 3, 5, 7, 9, or 11 and m is 10,000 to 50,000.

4. The liner of claim 2 further including a free-radical initiator comprising lauroyl peroxide or benzoyl peroxide and an acid scavenger comprising MgO, wherein the composition is curable under atmospheric conditions at about 100° C.

5. The liner of claim 1 wherein the cross-linking agent is ethylene glycol dimethacrylate.

6. The liner of claim 1 further including a filler in an amount up to about 30% by weight of the composition.

7. The liner of claim 6, wherein the filler comprises particles of a hard acrylic resin, fumed silica, or barium sulfate.

8. A liner of claim 7, wherein the filler comprises particles of a poly(methyl methacrylate) resin.

9. The liner of claim 8 wherein the fluoroelastomer is present in an amount of from about 30% to about 98%, the filler is present in an amount of from about 7% to about 30%, the cross-linking agent is present in an amount of from about 1% to about 12.5%, and the monomer is present in an amount of from about 1% to 40%, wherein all amounts are expressed in percent by weight of the composition.

* * * * *